United States Patent
Gholap et al.

(10) Patent No.: US 10,586,376 B2
(45) Date of Patent: Mar. 10, 2020

(54) AUTOMATED METHOD OF PREDICTING EFFICACY OF IMMUNOTHERAPY APPROACHES

(71) Applicant: OptraScan, Inc., Cupertino, CA (US)

(72) Inventors: Abhijeet Gholap, Cupertino, CA (US); Anagha Jadhav, Cupertino, CA (US); Gurunath Kamble, Cupertino, CA (US)

(73) Assignee: OPTRASCAN, INC., Cupertino, CA (US)

( * ) Notice: Subject to any disclaimer, the term of this patent is extended or adjusted under 35 U.S.C. 154(b) by 153 days.

(21) Appl. No.: 16/008,018

(22) Filed: Jun. 13, 2018

(65) Prior Publication Data

US 2018/0357816 A1 Dec. 13, 2018

Related U.S. Application Data

(60) Provisional application No. 62/518,731, filed on Jun. 13, 2017.

(51) Int. Cl.
*G06K 9/00* (2006.01)
*G06T 15/08* (2011.01)
(Continued)

(52) U.S. Cl.
CPC ......... *G06T 15/08* (2013.01); *G01N 33/5091* (2013.01); *G06K 9/00127* (2013.01);
(Continued)

(58) Field of Classification Search
CPC ... G06T 15/08; G06T 7/11; G06T 7/10; G06T 7/0012; G06T 7/0014; G06T 7/0016; G06T 7/174; G06T 7/337; G06T 7/40; G06T 2207/10056; G06T 2207/30024; G06T 2207/30004; G06T 2207/20076; G06T 2207/20081; G06T 2207/20084; G06T 2207/30096; G06K 9/00147; G06K 9/00127; G06K 9/46; G06K 9/6267; G06K 9/6269; G06K 9/6277; G06K 9/6284; G06K 2209/05; G01N 33/5091; G01N 33/57484;
(Continued)

(56) References Cited

U.S. PATENT DOCUMENTS

| | | | |
|---|---|---|---|
| 2015/0347702 A1* | 12/2015 | Chukka | G01N 33/57415 702/19 |
| 2016/0341731 A1* | 11/2016 | Sood | G16B 40/00 |

(Continued)

*Primary Examiner* — Jose L Couso (57) ABSTRACT

In an automated method of determining potential efficacy of immunotherapy approaches, an automated slide scanning system with an image acquisition unit is provided. A sample slide with a mounted tissue sample is received by the automated slide scanning system. One or more slide images of the tissue sample are acquired with the image acquisition unit. At least one cell segmentation process is executed on the slide image in order to identify tissue cells. The cells are analyzed with at least one cell classification algorithm in order to identify a tumor cell percent positivity value and an immune cell percent positivity value, and a treatment efficacy score is subsequently calculated. Further features provided include pixel to pixel image registration, reconstruction, composite multi-layer viewing, and other image management tools.

14 Claims, 6 Drawing Sheets

(51) Int. Cl.
  *G06T 7/10* (2017.01)
  *G01N 33/50* (2006.01)
  *G06T 7/00* (2017.01)
  *G06T 7/11* (2017.01)
  *G01N 15/14* (2006.01)
  *G01N 15/10* (2006.01)

(52) U.S. Cl.
  CPC ........ *G06K 9/00147* (2013.01); *G06T 7/0012* (2013.01); *G06T 7/10* (2017.01); *G06T 7/11* (2017.01); *G01N 15/1475* (2013.01); *G01N 2015/1006* (2013.01); *G01N 2800/60* (2013.01); *G06T 2207/10056* (2013.01); *G06T 2207/30004* (2013.01); *G06T 2207/30024* (2013.01)

(58) Field of Classification Search
  CPC ........... G01N 15/1475; G01N 2800/60; G01N 2800/52; G01N 2015/1006; G16H 50/30; G16H 50/70; G16H 50/80; G16H 50/20; G16H 50/50; G16H 10/60; G16H 30/40; G06Q 50/24; Y02A 90/26; C12Q 1/6886; C12Q 2600/154; G16B 20/00; G16B 40/00; A61B 5/4842; A61B 5/4848; A61B 5/7264; A61B 5/7267; A61B 6/50; A61K 49/0004

See application file for complete search history.

(56) References Cited

U.S. PATENT DOCUMENTS

| | | | |
|---|---|---|---|
| 2017/0285029 A1* | 10/2017 | Hanks | G01N 33/57407 |
| 2018/0242906 A1* | 8/2018 | Madabhushi | G06K 9/6284 |
| 2018/0253591 A1* | 9/2018 | Madabhushi | G06K 9/00147 |
| 2018/0253841 A1* | 9/2018 | Madabhushi | G06T 7/0012 |
| 2018/0336395 A1* | 11/2018 | Madabhushi | G06K 9/00147 |
| 2019/0087693 A1* | 3/2019 | Madabhushi | G06K 9/6277 |
| 2019/0258855 A1* | 8/2019 | Madabhushi | G06T 7/0012 |

* cited by examiner

AUTOMATED METHOD OF PREDICTING EFFICACY OF IMMUNOTHERAPY APPROACHES

The current application claims a priority to the U.S. Provisional Patent application Ser. No. 62/518,731 filed on Jun. 13, 2017.

FIELD OF THE INVENTION

The present invention relates generally to digital pathology. More particularly, the present invention relates to image acquisition and analysis of biological specimens.

BACKGROUND OF THE INVENTION

The present invention relates to a consolidated system comprising various sectors of Digital Pathology which include whole slide scanning of biological specimens, image acquisition, image management and image interpretation/analysis using image analysis algorithms for detection of histological and immunohistochemical biomarkers, thereby aiding pathologists to draw improved and more accurate diagnosis of the pathological condition, and giving way to clinical development in immuno oncology with strong emphasis on specific immune regulatory checkpoints.

These hallmarks suggest that similar to the immune response they seek to measure, immune-biomarkers are diverse and inducible. Numerous factors are simultaneously engaged within the tumor microenvironment. Therefore, the presence or absence of any single immune-biomarker, including PD-L1, does not fully define immune status. Evaluating multiple immune-biomarkers in combination may provide a more accurate and comprehensive assessment. With respect to other FDA approved assays, further studies have shown that protein expressions on tumor infiltrating immune cells may predict response to immunotherapy better than on tumor cells alone. These tests are optimized to a threshold value based upon the number of cells demonstrating the protein expression on tumor cell (TC) and or immune cell (IC) membranes at or above the defined threshold intensity. However, evaluation of biomarker expression in lymphoid and other immune effector cells is a special challenge for pathologists. The above methods are implemented manually and experience to date has shown that interpretation by pathologists is more feasible and more reproducible for tumor cells than for infiltrating immune cells.

Immuno-oncology is based on the principle of provoking the patient's own immune system to boost an antitumor immune response in order to control or eradicate cancer cells. The recent advancements in immuno-oncology focusing on several specific immune regulatory checkpoints, one of which includes Programmed Death Ligand—1, has resuscitated the field of immune oncology. However, evaluation of multiple immune-biomarkers in combination with high resolution imaging offered by digital pathology with complex object recognition algorithms will provide a more comprehensive assessment and an aid for the pathologists to provide more accurate quantification of biomarkers. This will also help refine the understanding of converging immune and oncology pathways.

Digital Pathology offers captivating features which include a platform for image acquisition, image viewing, image interpretation, image analysis, image management and archival.

While all the above features/functions are available on separate platforms, there still lies a challenge in integrating/collaborating each of them on a single platform, supporting whole slide scanning, registration, segmentation and quantification of cancer cells based on biomarker content, thus opening the pathways to aid immuno oncology development.

US Patent No: 2012/0069049 A1 explains co-registration of multiple images, wherein two or more selected images may be automatically oriented for simultaneous viewing or automatically matched location on a reference image.

However there remains a need for an algorithm that addresses the following issues:

1. Fully automated analytics application integrated into whole slide scanner as the slide is being scanned without using a third party software as a holistic immuno-oncology tool
2. Fully automated analytics application integrated into whole slide scanner on a whole slide image or registered images stained with multiple biomarkers to facilitate 2D reconstruction and analytics
3. Fully automated analytics application integrated into whole slide scanner on serial sections yielding multiple whole slide images to facilitate 3D reconstruction and analytics

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

The present invention is a method of predicting the potential effectiveness of one or more immunotherapy approaches in a given patient through automated slide scanning and image analysis of a tissue sample from the patient. Analysis of one or more images acquired of a tissue sample mounted on a sample slide will provide insight into the likelihood of treatment efficacy through recognition and analysis of various biomarkers identified in the tissue sample. The present invention provides a consolidated system of various sectors: whole slide scanning, image acquisition, image management, and image interpretation and analysis through various algorithms, all geared towards quantifiably determining the probability a given patient will respond positively to a given immunotherapy treatment. Various algorithms utilized by the present invention may be trained through machine learning to ensure more accurate results.

The preferred embodiment of the present invention will include an intuitive hardware and software setup for automated slide scanning, image analysis and cell-based quantification. The system will provide operational tools for image segmentation and analysis on whole slides and/or regions of interest. A tumor tissue sample of any tumor type can be selected from a patient and immunostained by using any approved methods of detection that can be expressed on tumor and/or immune cells. Immunohistochemistry (IHC) is a conventional process of antigen/protein detection in a tissue section by using the principle of antigen antibody interaction. Thus, Immunohistochemical staining allows visualizing an antibody-antigen complex that can be implemented either by conjugating an antibody to peroxidases, to a color-producing reaction. Alternatively, the antibody can also be tagged to a fluorophore, such as but not limited to fluorescein or rhodamine. Typically, the antibodies are specific for a protein expressed by tumor and/or an immune cell surface marker. The tumor tissue sample may consist of, but is not limited to, a biopsy, resection sample, or metastatic tissue sample including lymphoid follicles.

After immunostaining next step is to digitize the slide(s) by using a high resolution slide scanning system whereby a digital image can be obtained to perform image analysis with the ability to save image/s in single and composite views, with the option of saving both individual and merged composite images simultaneously. The system will support multiple IHC image datasets and will not be limited to data size.

The preferred embodiment of the present invention will further comprise a quantification method for assessment of tumor and immune cells in a heterogeneous population of tumor microenvironment. Single or multiple biomarkers can be detected with quantification either in a single tissue slide stained simultaneously or in serial sections using multiple biomarkers of interest during implementation of the process. Multiphase, intensity and morphology based segmentation may be used for identification of all viable nucleated cells in the whole slide image. A distance transform algorithm may be applied on segmented image(s) to get seed points for further segmentation so as to separate as many connected cells as possible. Segmentation algorithms and/or steps may include:

Segregation of nests of cells into tumor and stromal/non-tumor regions.
Segmentation of positive tumor and immune cells with positive membrane staining.
Classification of cells into Normal cells/nuclei, Tumor cells/nuclei, Macrophages, Lymphocytes (immune cell population).
Shape, intensity, texture features based classification. For example, features like Nucleo: Cytoplasmic ratio, size, stained membrane is used for identifying and differentiating macrophages from tumor cells amongst a mixed population of tumor and immune cells in the whole slide image.
The cells are clustered (based on Euclidean distance between centers) as Tumor/Normal cells or immune (Lymphocytes).
Scores are generated as: Percent positivity of tumor cells and percentage positivity of immune cells separately.

Methods as disclosed above apply analysis of the slice of tissue section for defining the tumor and the non-tumor regions can be implemented either manually or by appropriate software methods. Software enables multi-level cell segmentation for the tumor and tumor microenvironment by applying high-fidelity single or compound masking algorithms using dedicated images that identify different cellular and subcellular structures of interest, comprehensive feature extraction and robust quantitative analysis. The cells assessed can be further quantified into tumor cells and immune cells as follows:

total number of tumor cells with positive and negative membrane staining
total number of tumor cells with positive membrane stained
total number of positive and negative membrane immune cells
total number of immune cells with positive membrane stained The automated detection, i.e. in the whole slide section on the digital image may be marked manually by a skilled technician, pathologist, pathology assistant or may be implemented in a fully automated manner as a Companion Research solution.

Cell segmentation should be scalable: the software shall enable importing of standard segmentation algorithms, user-specified and software validated segmentation algorithms.

The software may perform multi-level cell segmentation automatically and with user tunable parameters as per biomarker selection, with overlay for user validation. The software facilitates an interactive widget to display the accepted cellular features for segmentation of cells/features of interest. The software also provides an option to save and load the saved segmentation which can be applied for whole slide image analysis. The quantification results can be further exported in file formats compatible with 3rd party software for report generation.

The software also provides an interactive widget to display graphically the cellular features accepted by the user which is interactive to visualize the associated cell images in an image tray and vice versa with associative back gating of image analysis data to original high-resolution images.

Feature extraction: Comprehensive feature extraction for each biomarker is identified and plot features of the cells seen in the imagery for every cell including intensity, location, cell shape, cell texture In general, referring to FIG. 1, in the method of the present invention, an automated slide scanning system is provided, in addition to a processing device (Step A). The automated slide scanning system comprises an image acquisition unit, and the automated slide scanning system is electronically connected to the processing device. A sample slide is received through the automated slide scanning system (Step B), wherein a tissue sample is mounted to the sample slide. The tissue sample mounted to the sample slide may be understood to be from a patient for whom potential efficacy of one or more immunotherapy treatments is desired to be determined through the present invention. At least one slide image of the tissue sample is then acquired through the image acquisition unit (Step C). The at least one slide image may be, but is not limited to, a single whole slide image, multiple images of smaller regions of the tissue sample to be registered together, or other image configurations of the tissue sample as desired. Subsequently, at least one cell segmentation process is executed on the slide image through the processing device in order to identify a plurality of cells from the slide image (Step D). The plurality of cells is analyzed with at least one cell classification algorithm through the processing device in order to identify a tumor cell percent positivity value and an immune cell percent positivity value (Step E). A treatment efficacy score is then calculated from the tumor cell percent positivity value and the immune cell percent positivity value (Step F).

Figure 1:
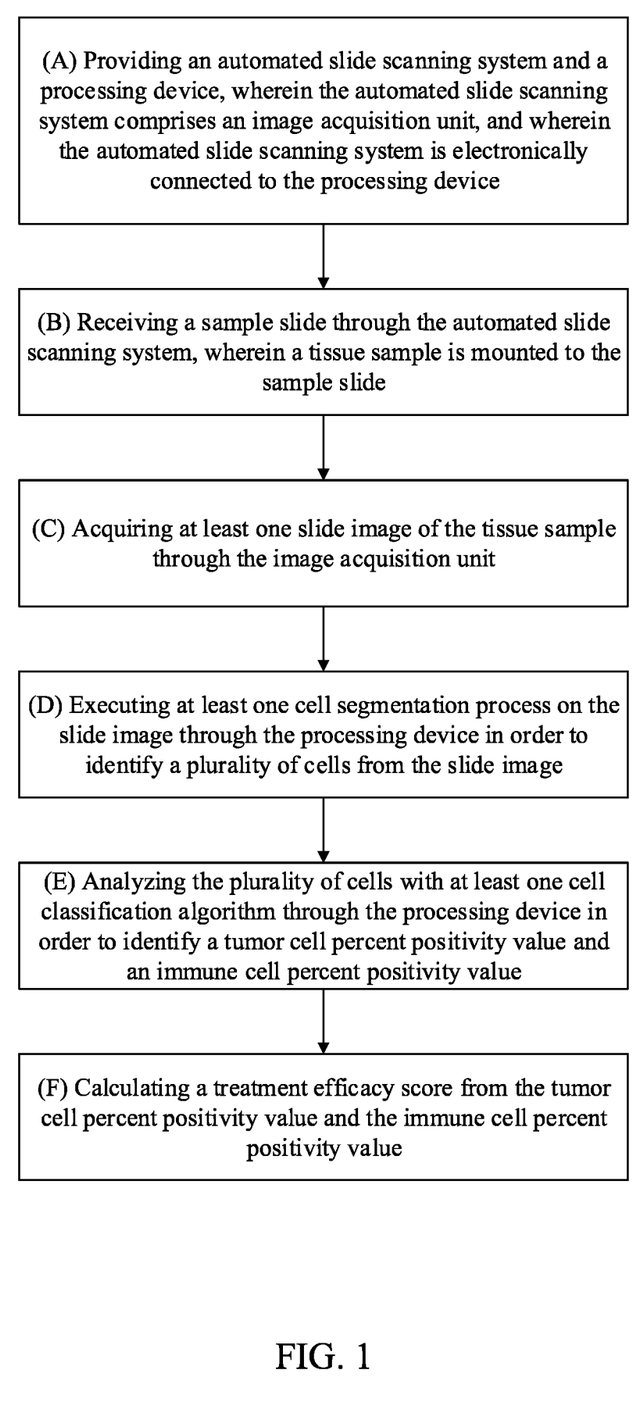
FIG. 1 is a stepwise flow diagram illustrating the general steps in the method of the present invention.

In some embodiments of the present invention, the plurality of cells is analyzed with at least one cell classification algorithm through the processing device in order to identify at least one biomarker.

Figure 2:
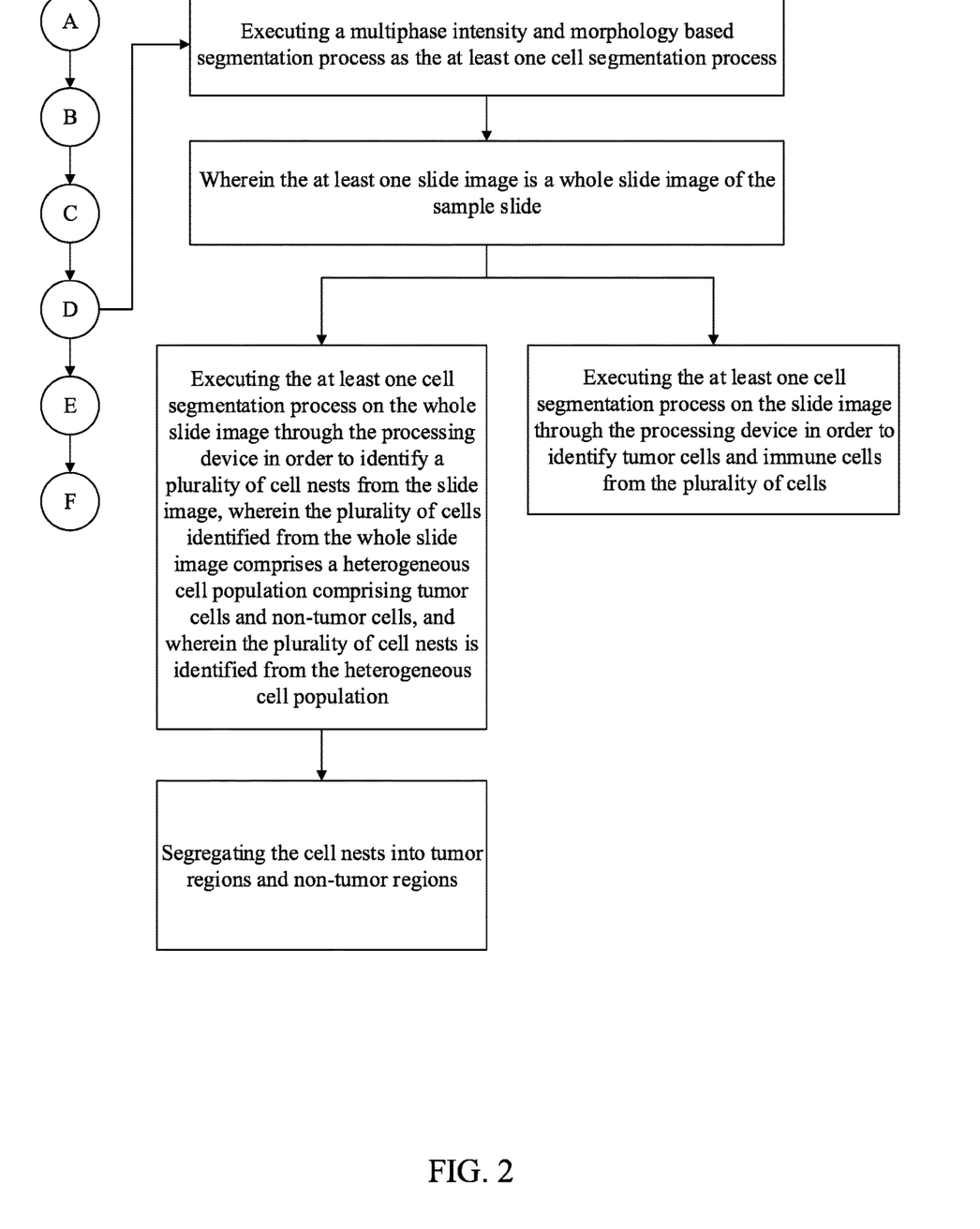
FIG. 2 is a stepwise flow diagram illustrating steps for executing cell segmentation processes.

In some embodiments, a multiphase intensity and morphology based segmentation process is executed as the at least one cell segmentation process, as illustrated in FIG. 2. In some embodiments, a cell and membrane segmentation process is executed as the at least one cell segmentation process. It should be noted that in various embodiments, various embodiments of segmentation processes may be utilized in sequence, in combination, or separately, depending on the desired result.

In some embodiments, wherein the at least one slide image is a whole slide image of the sample slide, at least one cell segmentation process is executed on the whole slide image through the processing device in order to identify a plurality of cell nests from the slide image, wherein the plurality of cells identified from the whole slide image comprises a heterogeneous cell population comprising tumor cells and non-tumor cells, and wherein the plurality of cell nests is identified from the heterogeneous cell population. The cell nests are further segregated into tumor regions and non-tumor regions. More particularly, the at least one cell segmentation process may be executed on the slide image through the processing device in order to identify tumor cells and immune cells from the plurality of cells.

Figure 3:
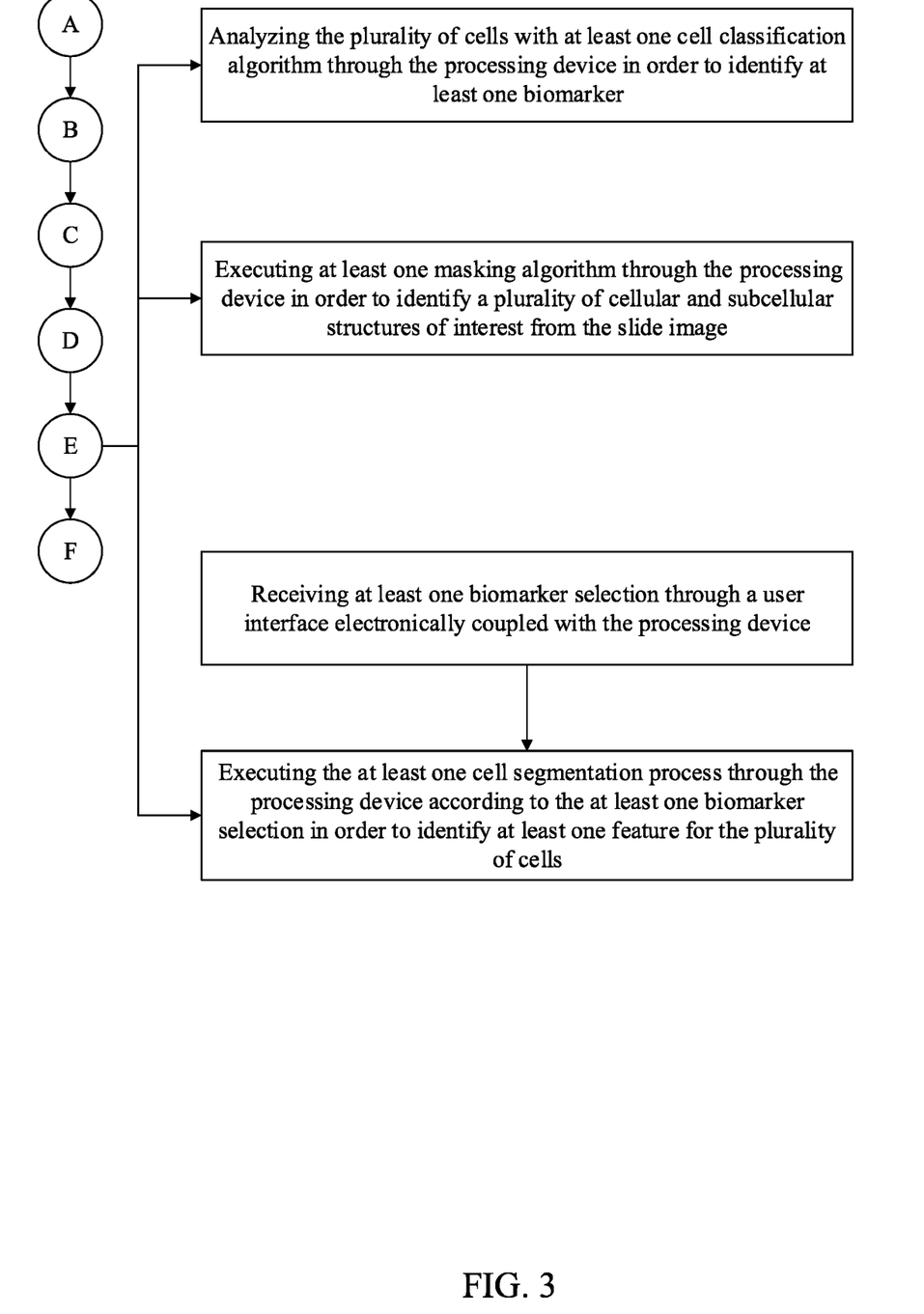
FIG. 3 is a stepwise flow diagram illustrating steps for analyzing slide images.

As shown in FIG. 3, in some embodiments, at least one masking algorithm may be executed through the processing device in order to identify a plurality of cellular and subcellular structures of interest from the at least one slide image, wherein the at least one slide image may comprise a series of images or a single whole slide image in various embodiments.

In some embodiments, a user is able to select from multiple biomarkers they wish to manually examine through the present invention. Thus, at least one biomarker selection may be received through a user interface electronically coupled with the processing device. The at least one cell segmentation process is then executed through the processing device according to the at least one biomarker selection in order to identify at least one feature for the plurality of cells, wherein the at least one feature corresponds with the at least one biomarker selection.

Figure 4:
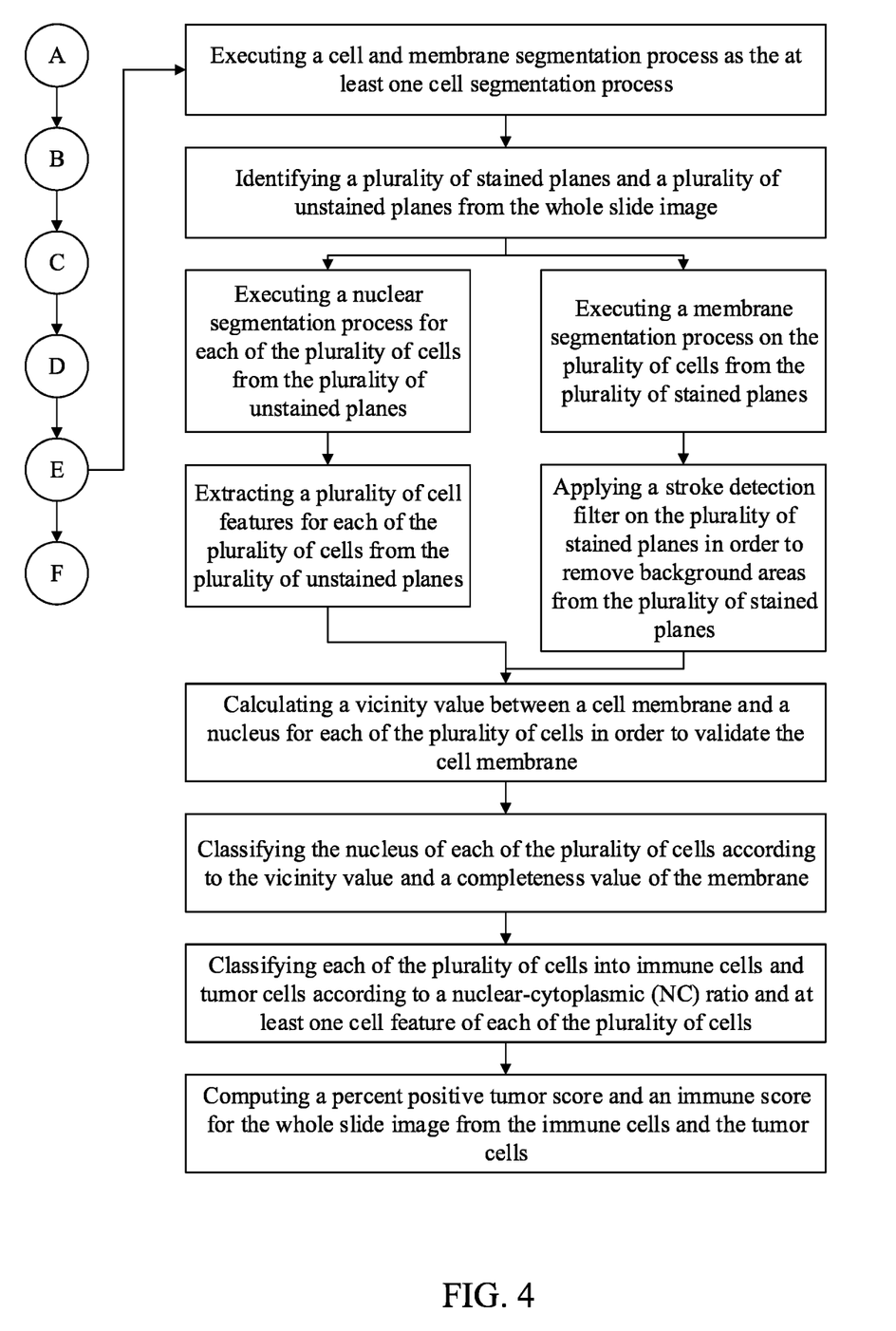
FIG. 4 is a stepwise flow diagram illustrating steps for executing a cell and membrane segmentation process.

Referring to FIG. 4, as previously mentioned, in some embodiments, a cell and membrane segmentation process is executed as the at least one cell segmentation process. An exemplary description of such a process is as follows. To engage in such a process, it is desirable in various instances that the at least one slide image is a whole slide image of the sample slide. A plurality of stained planes and a plurality of unstained planes are identified from the whole slide image using the processing device. A nuclear segmentation process is then executed for each of the plurality of cells from the plurality of unstained planes. A plurality of cell features for each of the plurality of cells is extracted from the plurality of unstained planes. A membrane segmentation process is executed on the plurality of cells from the plurality of stained planes. A stroke detection filter may be applied on the plurality of stained planes in order to remove background areas from the plurality of stained planes. A vicinity value may be calculated between a cell membrane and a nucleus for each of the plurality of cells in order to validate the cell membrane. The nucleus of each of the plurality of cells may be classified according to the vicinity value and a completeness value of the membrane. Each of the plurality of cells is classified into immune cells and tumor cells according to a nuclear-cytoplasmic (NC) ratio and at least one cell feature of each of the plurality of cells. Finally, a percent positive tumor score and an immune score are computed for the whole slide image from the immune cells and the tumor cells.

The preferred embodiment of the present invention provides image registration capabilities. The system provides pixel to pixel registration of all accumulated images acquired of the same slide(s) after staining the slide with a panel of immunostains with a reset/undo function. The present invention will also provide image registration for 2D reconstruction from serial sections with visualization of images acquired from single or multiple tissue specimens. The software allows the user to select two or more images that need to be registered pixel to pixel when the user loads two or more acquired images from the dataset in the user interface with the ability to manipulate the individual and registered image(s). These may include the same section with multiple rounds of staining or a full set of serial sections stained with the biomarkers of interest with no restriction on the number of sections imaged or image size. Automatic or manual registration can be applied on all these sections which can be user defined areas or whole tissue sections.

The software viewer should be able to display all acquired images as a multi-layer composite that can be selected in any combination of individual images and pseudo colors wherever applicable to facilitate user validation and display. The software also provides an option for splitting multicolor composite images either in a single tissue section or multiple sections including serial sections with appropriate naming.

Figure 5:
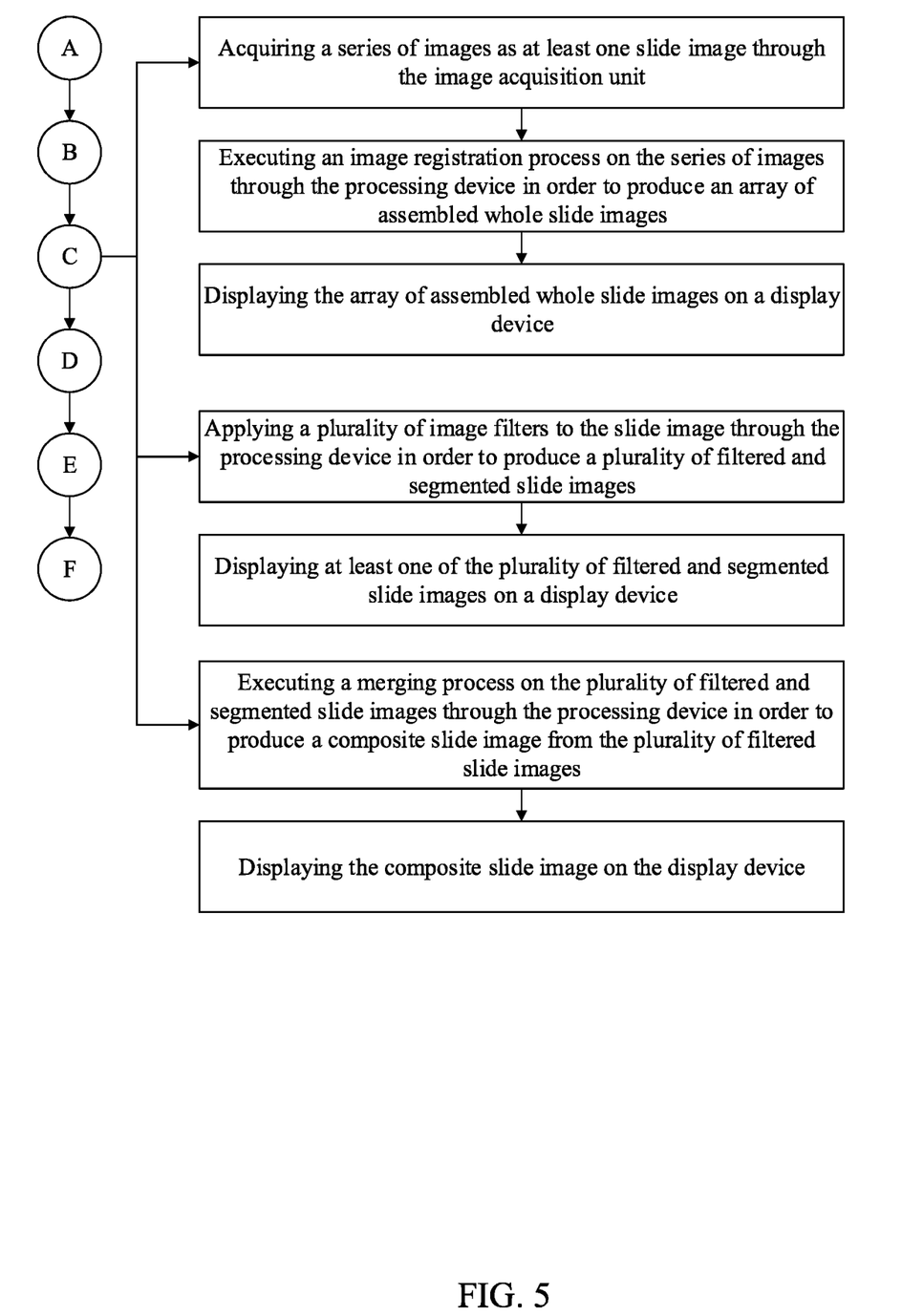
FIG. 5 is a stepwise flow diagram illustrating steps for image registration and viewing.

Referring to FIG. 5, in some embodiments, the at least one slide image may be acquired as a series of images through the image acquisition unit. In some embodiments, each of the series of images may cover a small portion of the entirety of the tissue sample mounted to the slide in order to achieve a desired resolution for the images. The series of images may further be stitched together in order to produce a whole slide image or similar end result. More particularly, an image registration process may be executed on the series of images through the processing device in order to produce an array of assembled whole slide images. The array of assembled whole slide images may further be displayed on a display device for inspection by a user.

As previously disclosed, in various embodiments of the present invention, various processes are executed upon the at least one slide image captured through the slide scanning assembly in order to manipulate the slide images to emphasize and/or identify various characteristics of the tissue sample being analyzed, such as cell groups, tumor and non-tumor cell regions, cell membranes, nuclei, various biomarkers, and other characteristics. It should be understood that any algorithm or combination of algorithms, well-known or newly developed in any relevant field, such as, but not limited to, immunochemistry, image manipulation, or other fields, may be applied through the present invention in order to manipulate slide images in the desired manner. In some embodiments, a plurality of image filters may be applied to the slide image through the processing device in order to produce a plurality of filtered and segmented slide images, and at least one of the plurality of filtered and segmented slide images may be displayed on a display device for manual user inspection. Furthermore, in some embodiments, a merging process may be executed on the plurality of filtered and segmented slide images through the processing device in order to produce a composite image from the plurality of filtered and segmented slide images, and the composite image may then be displayed on the display device.

Figure 6:
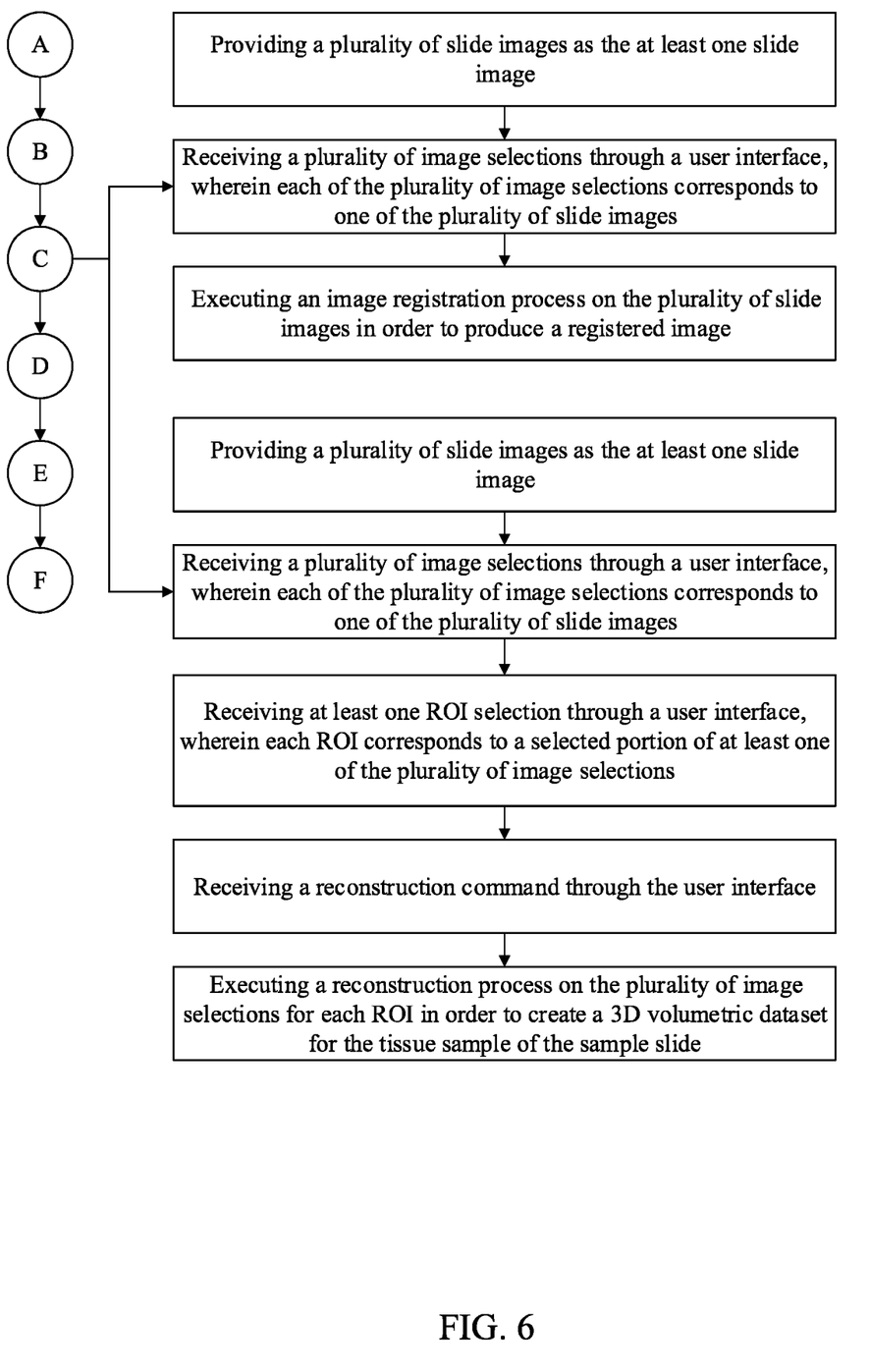
FIG. 6 is a stepwise flow diagram illustrating further steps for image registration and viewing.

Referring to FIG. 6, in some embodiments, wherein a plurality of slide images is acquired as the at least one slide image, a plurality of image selections may be received from a user through a user interface, wherein each of the plurality of image selections corresponds to one of the plurality of slide images. Subsequently, an image registration process may be executed on the plurality of slide images in order to produce a registered image.

In some embodiments, wherein a plurality of slide images is acquired as the at least one slide image, a plurality of image selections may be received through a user interface, wherein each of the plurality of image selections corresponds to one of the plurality of slide images. Subsequently, at least one ROI selection may be received through a user interface, wherein each ROI corresponds to a selected portion of at least one of the plurality of image selections. A reconstruction command may then be received through the user interface, and a reconstruction process may then be executed on the plurality of image selections for each ROI in order to create a three-dimensional (3D) volumetric dataset for the tissue sample of the sample slide.

Preferably, the present invention will provide image registration for 3D reconstruction from serial sections in whole slide imaging applications. An exemplary image registration process follows:

1) User selects multiple sections for 3D reconstruction from the dataset of the at least one slide image. These can include a full set of serial sections imaged from whole tissue sections with no restriction on the number of sections imaged or image size.

2) Automatic or manual registration may be applied on all these sections.

3) A user selects a single channel or multiple channels of the sections of interest, including serial sections to apply 3D reconstruction and draw Regions of interest (ROIs) on them. The ROIs can be either user-defined using standard drawing tools (resizable and repositionable rectangle, square, circle, ellipsoid, polygonal, freeform) for the acquired image datasets.

4) Once ROIs are drawn, the user can go for 3D Reconstruction by clicking a button ("3D") available on the user interface.

5) The user has the option to select a method for reconstruction using integrated reconstruction algorithms.

6) The process can be applied to any number of selected sections of interest as well as an entire array of serial sections imaged to create a 3D volumetric dataset for the tissue.

After completing the process, 3D surface will be rendered viewable with access to necessary widgets (tools: real-time Pan, Zoom, Rotate, and Measure cell counts and other parameters of interests in user-defined ROIs) to analyze 3D reconstructed data, with no restriction on the number of sections imaged or image size.

Although the invention has been explained in relation to its preferred embodiment, it is to be understood that many other possible modifications and variations can be made without departing from the spirit and scope of the invention as hereinafter claimed.

What is claimed is:

1. An automated method of predicting efficacy of immunotherapy approaches comprises the steps of:
  (A) providing an automated slide scanning system and a processing device, wherein the automated slide scanning system comprises an image acquisition unit, and wherein the automated slide scanning system is electronically connected to the processing device;
  (B) receiving a sample slide through the automated slide scanning system, wherein a tissue sample is mounted to the sample slide;
  (C) acquiring at least one slide image of the tissue sample through the image acquisition unit;
  (D) executing at least one cell segmentation process on the slide image through the processing device in order to identify a plurality of cells from the slide image;
  (E) analyzing the plurality of cells with at least one cell classification algorithm through the processing device in order to identify a tumor cell percent positivity value and an immune cell percent positivity value; and
  (F) calculating a treatment efficacy score from the tumor cell percent positivity value and the immune cell percent positivity value.

2. The automated method of determining potential efficacy of immunotherapy approaches as claimed in claim 1 comprises the step of:
  analyzing the plurality of cells with at least one cell classification algorithm through the processing device in order to identify at least one biomarker.

3. The automated method of determining potential efficacy of immunotherapy approaches as claimed in claim 1 comprises the step of:
  executing a multiphase intensity and morphology based segmentation process as the at least one cell segmentation process.

4. The automated method of determining potential efficacy of immunotherapy approaches as claimed in claim 1 comprises the steps of:
  wherein the at least one slide image is a whole slide image of the sample slide;
  executing the at least one cell segmentation process on the whole slide image through the processing device in order to identify a plurality of cell nests from the slide image, wherein the plurality of cells identified from the whole slide image comprises a heterogeneous cell population comprising tumor cells and non-tumor cells, and wherein the plurality of cell nests is identified from the heterogeneous cell population; and
  segregating the cell nests into tumor regions and non-tumor regions.

5. The automated method of determining potential efficacy of immunotherapy approaches as claimed in claim 1 comprises the steps of:
  wherein the at least one slide image is a whole slide image of the sample slide;
  executing the at least one cell segmentation process on the slide image through the processing device in order to identify tumor cells and immune cells from the plurality of cells.

6. The automated method of determining potential efficacy of immunotherapy approaches as claimed in claim 1 comprises the steps of:

executing at least one masking algorithm through the processing device in order to identify a plurality of cellular and subcellular structures of interest from the slide image.

7. The automated method of determining potential efficacy of immunotherapy approaches as claimed in claim 1 comprises the steps of:
receiving at least one biomarker selection through a user interface electronically coupled with the processing device; and
executing the at least one cell segmentation process through the processing device according to the at least one biomarker selection in order to identify at least one feature for the plurality of cells.

8. The automated method of determining potential efficacy of immunotherapy approaches as claimed in claim 1 comprises the step of:
executing a cell and membrane segmentation process as the at least one cell segmentation process.

9. The automated method of determining potential efficacy of immunotherapy approaches as claimed in claim 8 comprises the steps of:
providing that the at least one slide image is a whole slide image of the sample slide;
identifying a plurality of stained planes and a plurality of unstained planes from the whole slide image;
executing a nuclear segmentation process for each of the plurality of cells from the plurality of unstained planes;
extracting a plurality of cell features for each of the plurality of cells from the plurality of unstained planes;
executing a membrane segmentation process on the plurality of cells from the plurality of stained planes;
applying a stroke detection filter on the plurality of stained planes in order to remove background areas from the plurality of stained planes;
calculating a vicinity value between a cell membrane and a nucleus for each of the plurality of cells in order to validate the cell membrane;
classifying the nucleus of each of the plurality of cells according to the vicinity value and a completeness value of the membrane;
classifying each of the plurality of cells into immune cells and tumor cells according to a nuclear-cytoplasmic (NC) ratio and at least one cell feature of each of the plurality of cells; and
computing a percent positive tumor score and an immune score for the whole slide image from the immune cells and the tumor cells.

10. The automated method of determining potential efficacy of immunotherapy approaches as claimed in claim 1 comprises the steps of:
acquiring a series of images as at least one slide image through the image acquisition unit;
executing an image registration process on the series of images through the processing device in order to produce an array of assembled whole slide images; and
displaying the array of assembled whole slide images on a display device.

11. The automated method of determining potential efficacy of immunotherapy approaches as claimed in claim 1 comprises the steps of:
applying a plurality of image filters to the slide image through the processing device in order to produce a plurality of filtered and segmented slide images; and
displaying at least one of the plurality of filtered and segmented slide images on a display device.

12. The automated method of determining potential efficacy of immunotherapy approaches as claimed in claim 11 comprises the steps of:
executing a merging process on the plurality of filtered and segmented slide images through the processing device in order to produce a composite slide image from the plurality of filtered and segmented slide images; and
displaying the composite slide image on the display device.

13. The automated method of determining potential efficacy of immunotherapy approaches as claimed in claim 1 comprises the steps of:
providing a plurality of slide images as the at least one slide image;
receiving a plurality of image selections through a user interface, wherein each of the plurality of image selections corresponds to one of the plurality of slide images; and
executing an image registration process on the plurality of slide images in order to produce a registered image.

14. The automated method of determining potential efficacy of immunotherapy approaches as claimed in claim 1 comprises the steps of:
providing a plurality of slide images as the at least one slide image;
receiving a plurality of image selections through a user interface, wherein each of the plurality of image selections corresponds to one of the plurality of slide images;
receiving at least one ROI selection through a user interface, wherein each ROI corresponds to a selected portion of at least one of the plurality of image selections;
receiving a reconstruction command through the user interface; and
executing a reconstruction process on the plurality of image selections for each ROI in order to create a 3D volumetric dataset for the tissue sample of the sample slide.

* * * * *